United States Patent
Linder et al.

(10) Patent No.: US 11,369,799 B2
(45) Date of Patent: Jun. 28, 2022

(54) CONTACT FOR AN IMPLANTABLE MEDICAL DEVICE

(71) Applicant: Cardiac Pacemakers, Inc., St. Paul, MN (US)

(72) Inventors: William J. Linder, Golden Valley, MN (US); James Blilie, Shoreview, MN (US); Scott Dahl, St. Anthony Village, MN (US); Arthur J. Foster, Blaine, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 142 days.

(21) Appl. No.: 16/748,266

(22) Filed: Jan. 21, 2020

(65) Prior Publication Data

US 2020/0238090 A1    Jul. 30, 2020

Related U.S. Application Data

(60) Provisional application No. 62/796,956, filed on Jan. 25, 2019.

(51) Int. Cl.
*A61N 1/375* (2006.01)

(52) U.S. Cl.
CPC ....... *A61N 1/3752* (2013.01); *A61N 1/37512* (2017.08)

(58) Field of Classification Search
CPC .............. A61N 1/3752; A61N 1/37512; H01R 13/5219; H01R 43/16; H01R 2201/12
See application file for complete search history.

(56) References Cited

U.S. PATENT DOCUMENTS

| | | | |
|---|---|---|---|
| 7,055,812 B2 * | 6/2006 | Balsells | F16F 1/045 267/166 |
| 7,274,964 B2 | 9/2007 | Balsells | |
| 7,299,095 B1 | 11/2007 | Barlow et al. | |
| 8,500,499 B2 * | 8/2013 | Drew | H01R 13/187 439/843 |
| 2007/0282225 A1 * | 12/2007 | Terashi | A61M 25/09 600/585 |

(Continued)

FOREIGN PATENT DOCUMENTS

| | | |
|---|---|---|
| CN | 113365692 A | 9/2021 |
| WO | WO-2012027125 A1 | 3/2012 |
| WO | WO-2020154290 A1 | 7/2020 |

OTHER PUBLICATIONS

"International Application Serial No. PCT/US2020/014406, International Preliminary Report on Patentability dated Aug. 5, 2021", 7 pgs.

(Continued)

*Primary Examiner* — Catherine M Voorhees
(74) *Attorney, Agent, or Firm* — Schwegman Lundberg & Woessner, P.A.

(57) ABSTRACT

An apparatus includes a housing including a bore and a housing groove within the bore and located on an inner surface of the housing; and a coil spring located within the housing and mounted within the housing groove, wherein the housing groove has a non-uniform radius such that the coil spring defines zones of relative low contact force and zones of relative high contact force.

20 Claims, 5 Drawing Sheets

(56) References Cited

U.S. PATENT DOCUMENTS

| | | | | |
|---|---|---|---|---|
| 2012/0034804 A1* | 2/2012 | Smith | ................. | H01R 13/187 |
| | | | | 439/345 |
| 2013/0110204 A1 | 5/2013 | Lim et al. | | |
| 2013/0288501 A1* | 10/2013 | Russell | ............... | H01R 13/648 |
| | | | | 439/271 |
| 2016/0076568 A1 | 3/2016 | Dilmaghanian et al. | | |
| 2016/0134074 A1* | 5/2016 | Flynn | .................... | H01R 43/16 |
| | | | | 29/876 |
| 2018/0138633 A1* | 5/2018 | DeWitt | ............. | H01R 13/6277 |
| 2018/0278005 A1* | 9/2018 | Wang | .................. | H01R 13/187 |
| 2019/0058297 A1* | 2/2019 | Skubitz | ................. | H01R 13/44 |

OTHER PUBLICATIONS

"International Application Serial No. PCT/US2020/014406, International Search Report dated May 14, 2020", 4 pgs.
"International Application Serial No. PCT/US2020/014406, Written Opinion dated May 14, 2020", 5 pgs.

\* cited by examiner

CONTACT FOR AN IMPLANTABLE MEDICAL DEVICE

CLAIM OF PRIORITY

This application claims the benefit of priority under 35 U.S.C. § 119(e) of U.S. Provisional Patent Application Ser. No. 62/796,956, filed on Jan. 25, 2019, which is herein incorporated by reference in its entirety.

FIELD

This disclosure relates to implantable medical devices and more specifically to an electrical contact for an implantable medical device.

BACKGROUND

Leads implanted in or about the heart have been used to reverse certain life-threatening arrhythmia, or to stimulate contraction of the heart. Electrical energy is applied to the heart via electrodes on the leads to return the heart to normal rhythm.

A header on an implantable device is used to couple a conductor of the lead with circuitry within the implantable device. For instance, an electrical contact, such as a coil spring, in the header is used to electrically couple a cardiac stimulator system with the lead and electrode for making contact with a portion of the heart.

It is desirable that the connection between the lead and the header is mechanically and electrically reliable.

Overview

Example 1 can include subject matter that can include an apparatus including: a housing including a bore and a housing groove within the bore and located on an inner surface of the housing; and a coil spring located within the housing and mounted within the housing groove, wherein the housing groove has a non-uniform radius such that the coil spring defines zones of relative low contact force and zones of relative high contact force.

In Example 2, the subject matter of Example 1 can optionally include the housing groove defining an outer circumference having a non-circular shape.

In Example 3, the subject matter of Example 2 can optionally include the housing groove defining an outer circumference having a hexagon shape.

In Example 4, the subject matter of Example 2 can optionally include the housing groove defining an outer circumference having a rectangular shape with rounded corners.

In Example 5, the subject matter any of Examples 1-4 can optionally include the non-uniform radius of the housing groove physically constraining the relative high contact force zones of the coil spring to be positioned closer to a center of the bore relative to the relative low contact force zones of the coil spring.

In Example 6, the subject matter any of Examples 1-5 can optionally include the coil spring having a non-uniform winding.

In Example 7, the subject matter of Example 6 can optionally include the coil spring having periodic lengths of coil turns that have a larger diameter than adjacent coil turns.

In Example 8, the subject matter any of Examples 1-7 can optionally include the coil spring including a plurality of coil turns having an axial reduction of radius.

In Example 9, the subject matter any of Examples 1-8 can optionally include the housing groove defining a channel which is larger than the cross-section of the coil spring such that the coil spring can roll back and forth within the groove.

In Example 10, the subject matter any of Examples 1-9 can optionally include a lubricant located on the coil spring.

Example 11 can include subject matter that can include a header for an implantable medical device including: a header body including a passage to receive a terminal of an implantable lead; and a housing within the passage, the housing including a bore and a housing groove located on an inner surface of the housing; and a coil spring located within the housing and mounted within the housing groove and exposed to an interior of the housing so as to contact the terminal of the implantable lead mounted within the bore, wherein the housing groove has a non-uniform radius such that the coil spring defines zones of relative low contact force and zones of relative high contact force, wherein the non-uniform radius of the housing groove defines an outer housing groove surface that physically constrains the relative high contact force zones of the coil spring to be positioned closer to a center of the bore relative to the relative low contact force zones of the coil spring.

In Example 12, the subject matter of Example 11 can optionally include the housing groove defining an outer circumference having a non-circular shape.

In Example 13, the subject matter of Example 12 can optionally include the housing groove defining an outer circumference having a hexagon shape.

In Example 14, the subject matter of Example 12 can optionally include the housing groove defining an outer circumference having a rectangular shape with rounded corners.

In Example 15, the subject matter any of Examples 11-14 can optionally include the housing groove defining a channel which is larger than the cross-section of the coil spring such that the coil spring can roll back and forth within the groove.

Example 16 can include subject matter that can include an apparatus including: a housing including a bore and a housing groove within the bore and located on an inner surface of the housing; and a coil spring located within the housing and mounted within the housing groove, wherein the housing groove has a non-uniform radius such that the coil spring defines zones of relative low contact force and zones of relative high contact force.

In Example 17, the subject matter of Example 16 can optionally include the housing groove defining an outer circumference having a non-circular shape.

In Example 18, the subject matter of Example 17 can optionally include the housing groove defining an outer circumference having a hexagon shape.

In Example 19, the subject matter of Example 17 can optionally include the housing groove defining an outer circumference having a rectangular shape with rounded corners.

In Example 20, the subject matter any of Examples 16-19 can optionally include the non-uniform radius of the housing groove physically constraining the relative high contact force zones of the coil spring to be positioned closer to a center of the bore relative to the relative low contact force zones of the coil spring.

In Example 21, the subject matter any of Examples 16-20 can optionally include the coil spring having a non-uniform winding.

In Example 22, the subject matter of Example 21 can optionally include the coil spring having periodic lengths of coil turns that have a larger diameter than adjacent coil turns.

In Example 23, the subject matter any of Examples 16-22 can optionally include the coil spring including a plurality of coil turns having an axial reduction of radius.

In Example 24, the subject matter any of Examples 16-23 can optionally include the housing groove defining a channel which is larger than the cross-section of the coil spring such that the coil spring can roll back and forth within the groove.

In Example 25, the subject matter any of Examples 16-24 can optionally include a lubricant located on the coil spring.

Example 26 can include subject matter that can include a header for an implantable medical device including: a header body including a passage to receive a terminal of an implantable lead; and a housing within the passage, the housing including a bore and a housing groove located on an inner surface of the housing; and a coil spring located within the housing and mounted within the housing groove and exposed to an interior of the housing so as to contact the terminal of the implantable lead mounted within the bore, wherein the housing groove has a non-uniform radius such that the coil spring defines zones of relative low contact force and zones of relative high contact force, wherein the non-uniform radius of the housing groove defines an outer housing groove surface that physically constrains the relative high contact force zones of the coil spring to be positioned closer to a center of the bore relative to the relative low contact force zones of the coil spring.

In Example 27, the subject matter of Example 26 can optionally include the housing groove defining an outer circumference having a non-circular shape.

In Example 28, the subject matter of Example 27 can optionally include the housing groove defines an outer circumference having a hexagon shape.

In Example 29, the subject matter of Example 27 can optionally include the housing groove defining an outer circumference having a rectangular shape with rounded corners.

In Example 30, the subject matter any of Examples 26-29 can optionally include the coil spring having a non-uniform winding with periodic lengths of coil turns that have a larger diameter than adjacent coil turns.

In Example 31, the subject matter any of Examples 26-30 can optionally include the coil spring including a plurality of coil turns having an axial reduction of radius.

In Example 32, the subject matter any of Examples 26-31 can optionally include the housing groove defining a channel which is larger than the cross-section of the coil spring such that the coil spring can roll back and forth within the groove.

Example 33 can include subject matter that can include a method comprising: inserting a lead terminal into a passage of a header of an implantable device; and the lead terminal contacting a coil spring located within the header, wherein the coil spring defines zones of relative low contact force and zones of relative high contact force around a radius of the coil spring, wherein the coil spring is mounted within a housing groove on a housing within the header, and wherein the housing groove has a non-uniform radius.

In Example 34, the subject matter of Example 33 can optionally include wherein the housing groove defines an outer circumference having a non-circular shape.

In Example 35, the subject matter any of Examples 33-34 can optionally include applying a lubricant to the coil spring.

These examples can be combined in any permutation or combination. This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
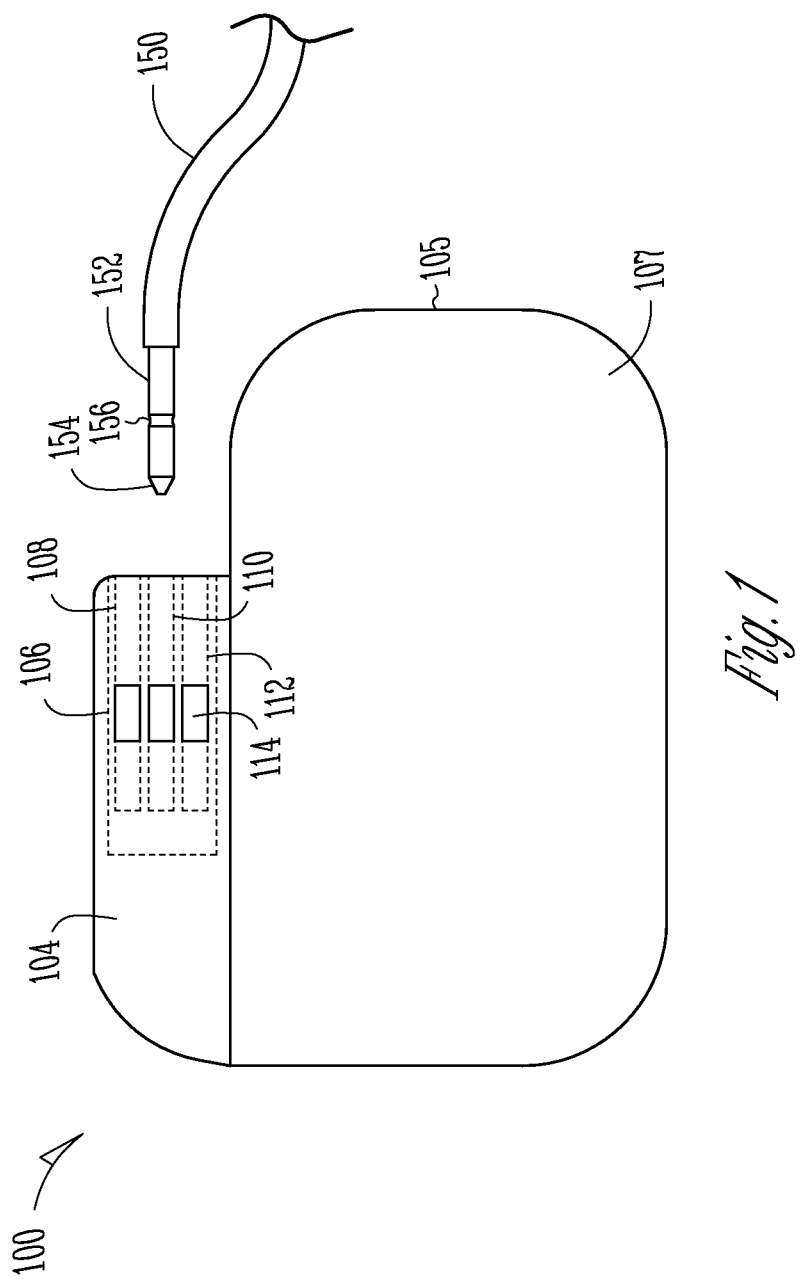
FIG. 1 shows a view of an implantable system according to at least one example.

FIG. 1 shows an implantable system 100, in accordance with one embodiment. The implantable system 100 includes a pulse generator 105 and at least one lead 150. The pulse generator 105 includes a housing 107 and a header 104 mounted to the housing 107. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include a power supply such as a battery, a capacitor, and other components housed in the housing 107. The pulse generator 105 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

In other embodiments, implantable system 100 can also be suitable for use with implantable electrical stimulators, such as, but not limited to, neuro-stimulators, skeletal stimulators, central nervous system stimulators, or stimulators for the treatment of pain.

The lead 150 includes a lead body having a proximal end, where a terminal 152 of the lead 150 can be coupled to the header 104 of the pulse generator 105. The lead 150 extends to a distal end, which can be coupled with a portion of a heart, when implanted. The distal end of the lead 150 includes at least one electrode which electrically couples the lead 150 with the heart. At least one electrical conductor is disposed within the lead 150 and extends from the proximal end to the electrode. The electrical conductor carries electrical currents and signals between the pulse generator 105 and the electrode.

The header 104 includes one or more passages 108, 110, 112 formed within a header core 106 and configured to receive the lead terminal 152 of the lead 150. In this example, the lead terminal 152 includes a proximal tip contact 154, and a ring contact 156. In other examples, the lead terminal 152 can include multiple ring contacts. The terminal contacts 154, 156 can be made of stainless steel while insulative portions of terminal 152 can be formed of polyurethane.

Within the header core 106 each of the one or more passages 108, 110, 112 can including one or more electrical contacts such as coil springs 114 (shown schematically) located within the passages 108, 110, 112. The coil springs 114 can be mounted within a housing located within the passages 108, 110, and 112. The coil springs 114 can be electrically connected to a feedthrough to electrically communicate between the lead 150 and the electronics within the pulse generator housing 107.

Presently, electrical contact reliability can be poor in some cases. A fundamental tradeoff with the existing designs is obtaining sufficient contact force while not compromising the lead insertion experience. For example, contact force is characterized in terms of Hertz stress. There is a Hertz stress window that takes into account both the materials and geometry of the actual contacting zones. Contact reliability is optimized when contact force falls inside the Hertz stress window.

Present coil spring are wound to provide a large number of similar contact points around the circumference of the lead terminal to coil spring connection. While it may seem to be intuitive that the large number of contacts that is provided in the present coil spring design would improve reliability, such is not the case. On the contrary, a few good contacts can outperform a large number of marginal ones. This is because sufficient force to make good contacts involving many contacts makes the lead insertion force prohibitively large. In other words, for a given insertion force budget, only a small number of contacts can be allocated sufficient contact force to operate the contact within the Hertz stress window.

Figure 2:
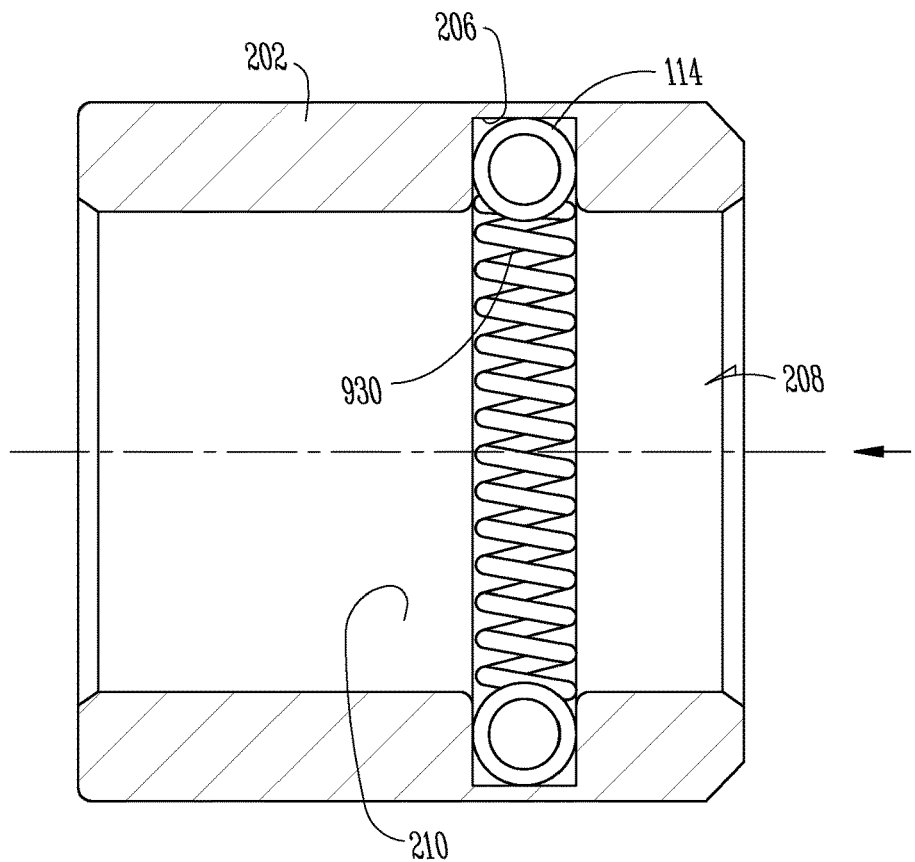
FIG. 2 shows a cross-section side view of housing including a coil spring, in accordance with one example.
Figure 3:
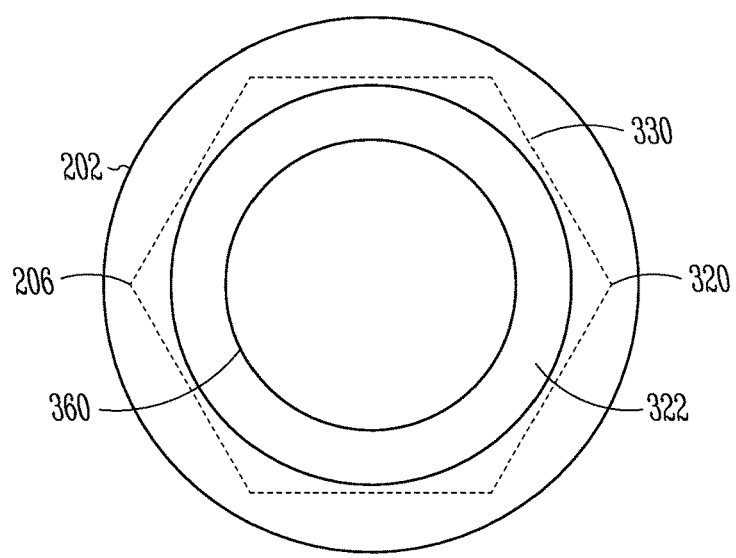
FIG. 3 shows a front schematic view of a coil spring housing, in accordance with one example.

One example of a coil spring design that allows for fewer contact points is shown in FIGS. 2-3. FIG. 2 shows a cross-section side view of a coil spring housing 202 including the coil spring 114, in accordance with one example. FIG. 3 shows a front schematic view of the coil spring housing 202, in accordance with one example.

The housing 202 includes a bore 208 and a housing groove 206 located on an inner surface 210 of the housing 202. The coil spring 114 is located within the housing 202 and mounted within the housing groove 206 and exposed to an interior of the housing 202 so as to contact a terminal of an implantable lead mounted within the bore 208.

In FIG. 3, the coil spring 114 is not shown but the coil spring 114 would be located between the housing groove 206 and a lead contact ring 360. Contact force redistribution can be achieved by modifying the shape of the housing groove that captures the contacting coil spring.

Here, the housing groove 206 has a non-uniform radius such that the coil spring 114 defines zones of relative low contact force 320 and zones of relative high contact force 322. The number and size of the various radii can vary as design parameters. Zones of low groove radius create regions of high contact force 322 and zones of large groove radius creates regions of low contact force 320.

The non-uniform radius of the housing groove 206 defines an outer housing groove surface 330 that physically constrains the relative high contact force zones 322 of the coil spring to be positioned closer to a center of the bore relative to the relative low contact force zones 320 of the coil spring. In this embodiment, the housing groove 206 defines an outer circumference having a hexagon shape. In other examples, the housing groove 206 defines an outer circumference having a variety of non-circular shapes.

In this example, by forming a non-uniform radius housing groove 206, the design allows for sufficient contact force, while not comprising the lead insertion experience. Moreover, the housing 202 and coil spring 114 fit within the mechanical envelope of the current header design and thus allow for minimal changes to the existing assembly process.

In one example, the housing 202 can be formed by machining or 3-D printing.

Figure 4:
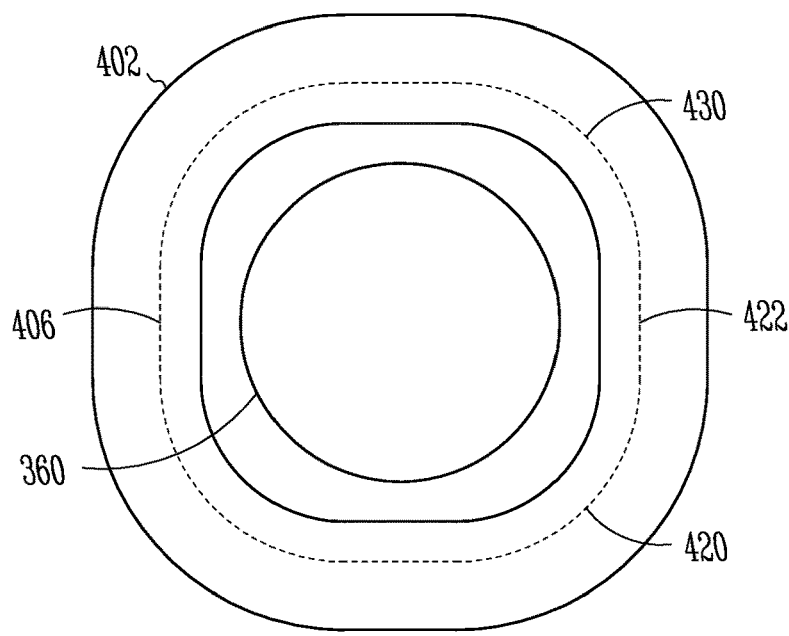
FIG. 4 shows a front schematic view of a coil spring housing, in accordance with one example.

FIG. 4 shows a front schematic view of a coil spring housing 402, in accordance with one example. Again, the coil spring is not shown but would occupy the space between a housing groove 406 and the lead contact ring 360. In this example, the housing groove 406 has a non-uniform radius such that the coil spring defines zones of relative low contact force 420 and zones of relative high contact force 422. Here, the housing groove 406 defines an outer circumference having a rectangular shape with rounded corners. As in the example above, the non-uniform radius of the housing groove 406 defines an outer housing groove surface 430 that physically constrains the relative high contact force zones 422 of the coil spring to be positioned closer to a center of the bore relative to the relative low contact force zones 420 of the coil spring.

In one example, the housing 402 can be formed by machining or 3-D printing a standard circular radius groove housing and then squeezing the housing with a tool to modify the shape of the housing groove that captures the contact spring.

Figure 5:
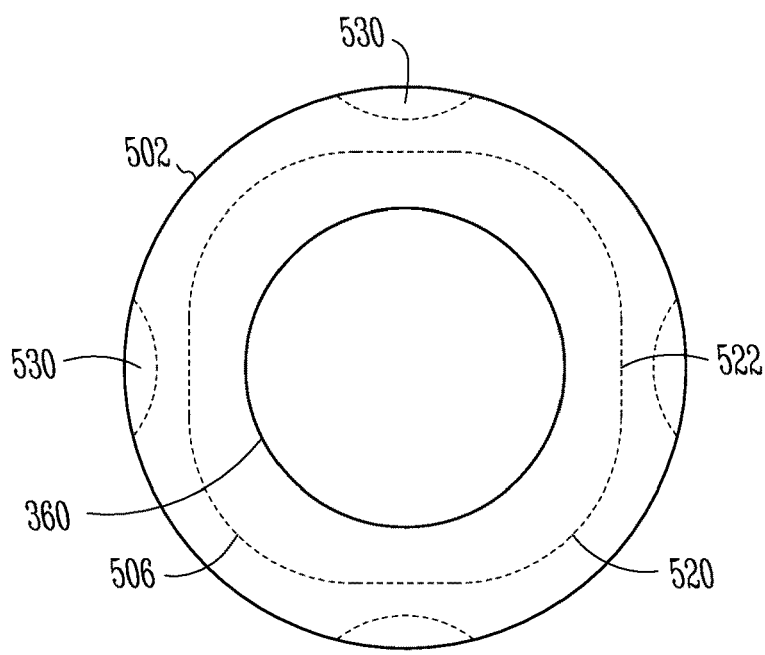
FIG. 5 shows a front schematic view of a coil spring housing, in accordance with one example.

FIG. 5 shows a front schematic view of a coil spring housing 502, in accordance with one example. Here, a housing groove 506 has a non-uniform radius such that the coil spring defines zones of relative low contact force 520 and zones of relative high contact force 522. As in the above example, the housing groove 506 defines an outer circumference having a rectangular shape with rounded corners.

Here, the housing 502 can be formed by machining or 3-D printing a standard circular radius groove housing and then "coining" the housing to form dimples 530 with a tool over the groove 506 in the housing 502 to create reduced radius portions of the housing groove 506.

Figure 6:
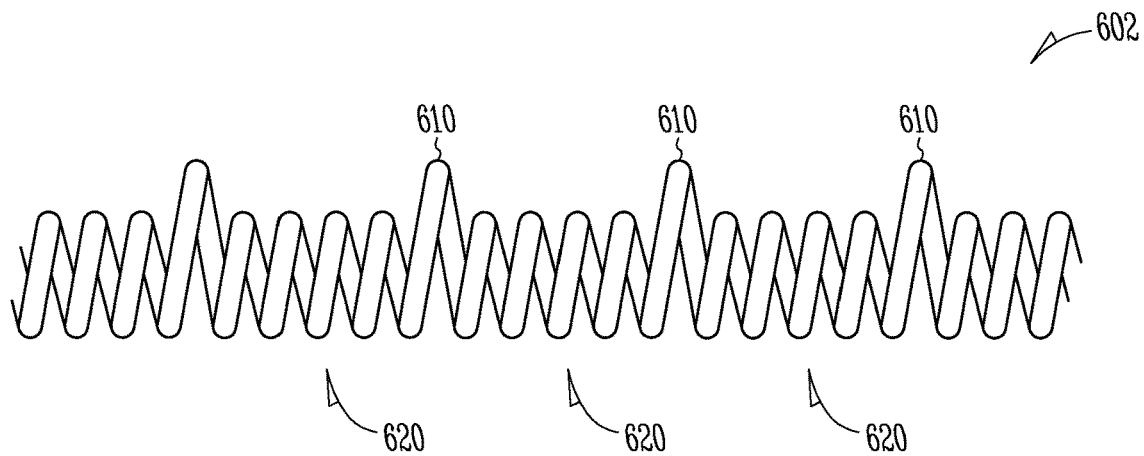
FIG. 6 shows a side view of an unwound coil spring, in accordance with one example.

FIG. 6 shows a side view of an unwrapped coil spring 602, in accordance with one example. Here, the coil spring 602 has a non-uniform winding. Specifically, the coil spring 602 has periodic lengths of coil turns 610 that have a larger diameter than adjacent coil turns 620. In this example, the center of raised turns 610 is shown off center, but this not required. Also, single raised turns are shown, but any number of consecutive raised, or normal turns can be used. When coil spring 602 is wrapped into a coil (such as coil spring 114, FIG. 2), the larger diameter coil turns 610 provide an area of relatively high contact force while the smaller diameter coil turns 620 provide an area of relatively low contact force.

Again, this provides for balancing between overall contact force between the lead and the contact spring and the insertion force needed.

In various examples, coil spring 602 can be used in a standard circular radius housing groove or can combined used with a non-uniform radius housing groove, such as in the examples discussed above.

In one example, to form the coil spring 602, a standard coil spring can be formed and then deformed mechanically so that coil turns 620 are pinched and coil turns 610 can be raised to create regions of higher contact force. The pinching zones defined by coil turns 620 create zones of lowered contact force depending on their orientation in the final assembly.

In another example the deformation by pinching can also be done in the final assembly with a fluted tool inserted into the housing bore and pinching the coil spring in the assembly radial dimension creating zones of lowered contact force. In another example, the coil spring 602 can be originally wound with a slightly larger diameter after every several turns of normal diameter.

Figure 7:
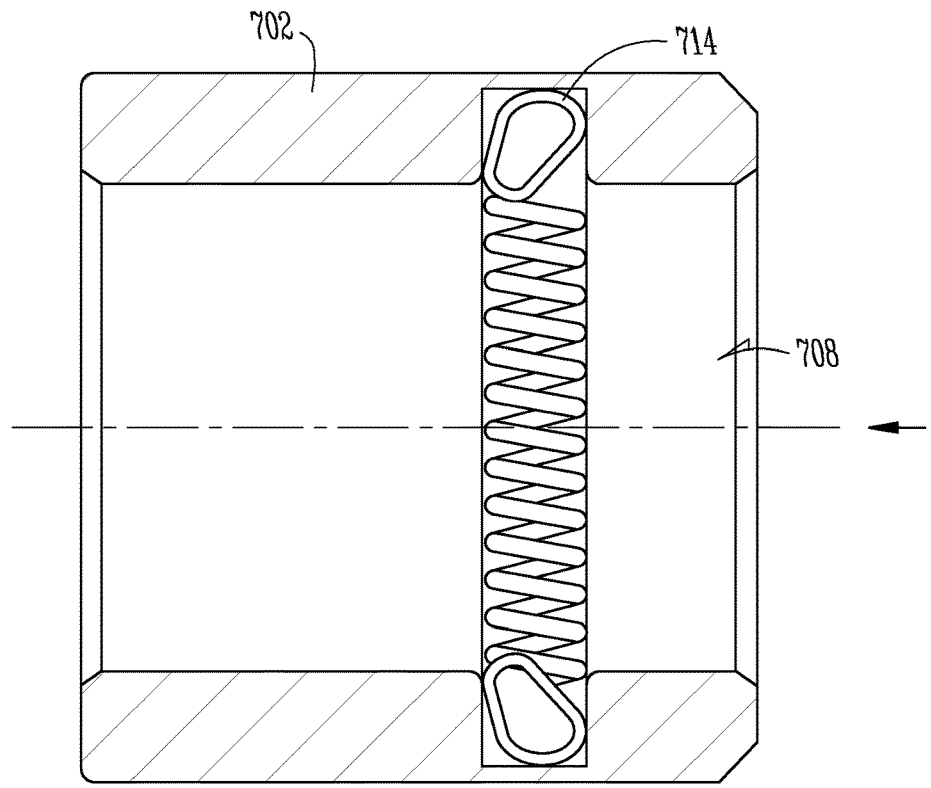
FIG. 7 shows a cross-section side view of a coil spring within a housing, in accordance with one example.
Figure 8:
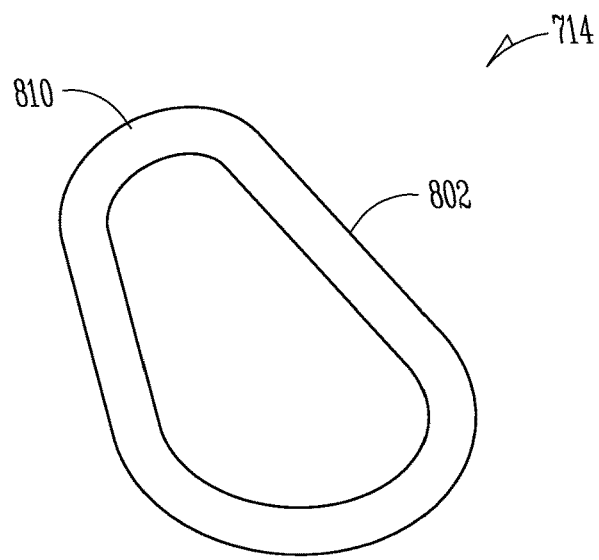
FIG. 8 shows a view of a coil turn of the coil spring of FIG. 7.

FIG. 7 shows a cross-section side view of a coil spring 714 within a housing 702, in accordance with one example. FIG. 8 shows a view of a coil turn 802 of the coil spring 714. Here, the coil spring 714 is shaped so as to define focused contact zones. In this example, contact force redistribution can be achieved by inserting a tool into a housing bore 708 which creates an axial reduction of the coil turn radius (using a taper tool, for example) in which an axial pinch-point 810 is obtained. Accordingly, the coil spring 714 wire cross section can focus contact forces into a smaller surface area at the axial pinch point 810. In this example, the coil spring 714 includes a plurality of coil turns 802 having an axial reduction of radius of the coil turns. Coil spring 714 can be either used alone or with any of the other examples herein. For example, the coil spring 714 can be used in either a uniform radius housing groove or a non-uniform radius housing groove and can be combined with the non-uniform winding of coil spring 602 (FIG. 6).

Figure 9:
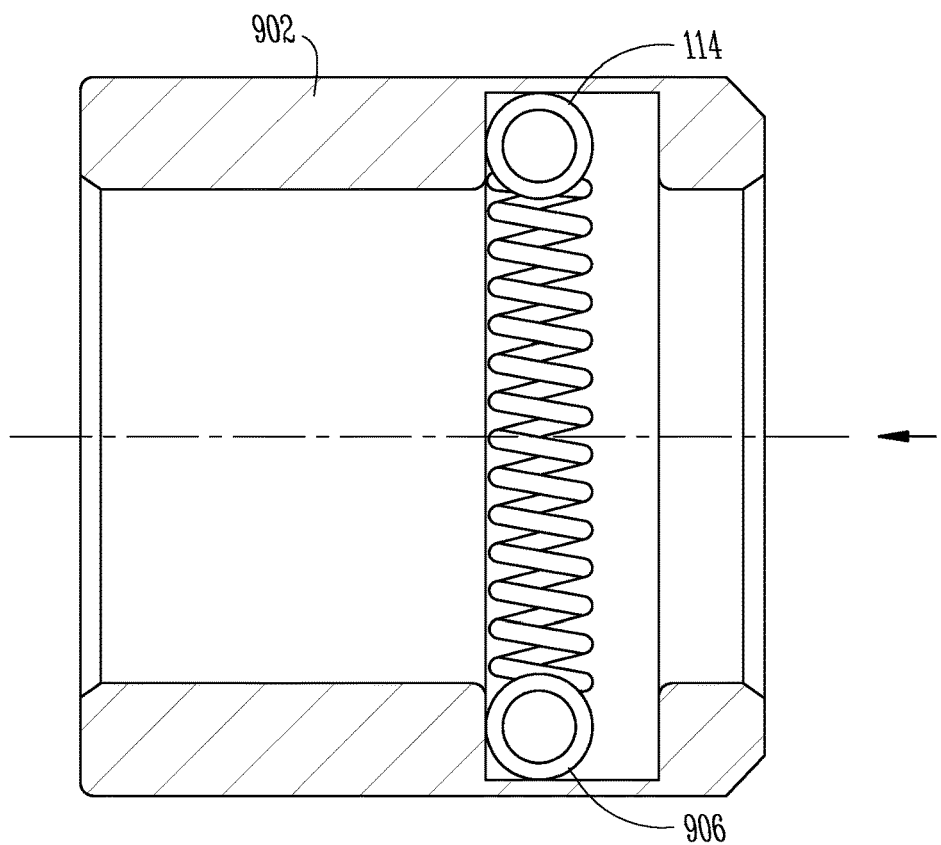
FIG. 9 shows a cross-section side view of a coil spring within a housing, in accordance with one example.

FIG. 9 shows a cross-section side view of the coil spring 114 within a housing 902, in accordance with one example. A housing groove 906 defines a channel which is larger than the cross-section of the coil spring 114 such that the coil spring can roll back and forth axially within the groove 906 allowing the connection to "float." This embodiment takes advantage of the coil spring's ability to roll rather than slide with axial motion and thus reduces fretting since the rolling reduces the ability of the lead to frictionally rub against the surface of the spring and breaking off oxides which lead to fretting. Moreover, allowing the coil spring 114 to roll within housing can assist insertion.

In some embodiments, this example can be combined with the other prior suggested approaches.

Referring back to any of the above embodiments a lubricant can be added to the coil spring. For example, the coil spring 114 in FIG. 2 can further include a lubricant 930 located on the coil spring 114. Lubricants can improve both fretting and insertion force. The lubricant can be applied to augment any of the contact ideas presented herein. The lubricant works by excluding oxygen from the contact zone (thus reducing oxidization and thus fretting) and by reducing sliding force. The lubricant chosen can be biocompatible, such as mineral oil or silicone oil. The lubricant can be applied at the contact component level of the assembly, or the lubricant can be applied to the final assembly. Moreover, lubricants reduce friction with lead insertion due to other sliding surfaces not directly related to the electrical contacts such as seal rings in the lead bore. Often these other terms represent the dominant portion of the lead insertion force budget.

In any of the examples herein, the coil spring wire shape can be symmetric or anti-symmetric, to balance the contact force versus surface area considerations. For example, the wire shape can be round, triangular, square, oval, rectangular or other shapes.

In one example use of the coil springs discussed herein, reference will be made to the example of FIGS. 1, 2, and 3. A method of inserting a lead terminal into a header can include inserting the lead terminal 152 into the passage 108 of the header 104 of the implantable device 100, and the lead terminal 152 contacting the coil spring 114 located within the header 104. The coil spring 114 defines zones of relative low contact force 320 and zones of relative high contact force 322 around a radius of the coil spring 114. The coil spring 114 can be mounted within the non-uniform radius housing groove 206 on the housing 202 within the header 104.

Among, the advantages of the above designs, the designs help balance the trade-off compromise of reliable contact vs trouble free insertion of the lead. Moreover, one advantage of the present designs are the designs herein fit inside the mechanical envelope of the current designs and allows minimal changes to existing assembly process.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to The claimed invention is:

1. An apparatus comprising:
   a housing including a bore and a housing groove within the bore and located on an inner surface of the housing; and
   a coil spring located within the housing and mounted within the housing groove, wherein, in a cross-sectional plane which is perpendicular to a longitudinal axis of the bore, the housing groove has a non-uniform radius around a circumference of the housing groove wherein a base of the groove includes a wall around a circumference of the groove, and radii extending from a center of the bore to the wall have varying lengths around the circumference in the cross-sectional plane which is perpendicular to the longitudinal axis of the bore so that the coil spring defines low contact force zones and high contact force zones relative to each other so that the high contact force zones apply a relatively higher force on a cylindrically shaped lead terminal inserted into the bore than the low contact force zones.

2. The apparatus of claim 1, wherein the housing groove defines an outer circumference having a non-circular shape.

3. The apparatus of claim 2, wherein the housing groove defines an outer circumference having a hexagon shape.

4. The apparatus of claim 2, wherein the housing groove defines an outer circumference having a rectangular shape with rounded corners.

5. The apparatus of claim 1, wherein the non-uniform radius of the housing groove physically constrains the relative high contact force zones of the coil spring to be positioned closer to a center of the bore relative to the relative low contact force zones of the coil spring.

6. The apparatus of claim 1, wherein the coil spring has a non-uniform winding.

7. The apparatus of claim 6, wherein the coil spring has periodic lengths of coil turns that have a larger diameter than adjacent coil turns.

8. The apparatus of claim 1, wherein the coil spring includes a plurality of coil turns having an axial reduction of radius.

9. The apparatus of claim 1, wherein the housing groove defines a channel which is larger than the cross-section of the coil spring such that the coil spring can roll back and forth within the groove.

10. The apparatus of claim 1, further including a lubricant located on the coil spring.

11. A header for an implantable medical device comprising:
   a header body including a passage to receive a terminal of an implantable lead; and
   a housing within the passage, the housing including a bore and a housing groove located on an inner surface of the housing; and
   a coil spring located within the housing and mounted within the housing groove and exposed to an interior of the housing so as to contact the terminal of the implantable lead mounted within the bore, wherein, in a cross-sectional plane which is perpendicular to a longitudinal axis of the bore, the housing groove has a non-uniform radius around a circumference of the housing groove wherein a base of the groove includes a wall around a circumference of the groove, and radii extending from a center of the bore to the wall have varying lengths around the circumference in the cross-sectional plane which is perpendicular to the longitudinal axis of the bore so that the coil spring defines low contact force zones and high contact force zones relative to each other so that the high contact force zones apply a relatively higher force on a cylindrically shaped lead terminal inserted into the bore than the low contact force zones, wherein the non-uniform radius of the housing groove defines an outer housing groove surface that physically constrains the relative high contact force zones of the coil spring to be positioned closer to a center of the bore relative to the relative low contact force zones of the coil spring.

12. The apparatus of claim 11, wherein the housing groove defines an outer circumference having a non-circular shape.

13. The apparatus of claim 12, wherein the housing groove defines an outer circumference having a hexagon shape.

14. The apparatus of claim 12, wherein the housing groove defines an outer circumference having a rectangular shape with rounded corners.

15. The apparatus of claim 11, wherein the coil spring has a non-uniform winding with periodic lengths of coil turns that have a larger diameter than adjacent coil turns.

16. The apparatus of claim 11, wherein the coil spring includes a plurality of coil turns having an axial reduction of radius.

17. The apparatus of claim 11, wherein the housing groove defines a channel which is larger than the cross-section of the coil spring such that the coil spring can roll back and forth within the groove.

18. A method comprising:
   inserting a cylindrical lead terminal into a passage of a header of an implantable device; and
   the lead terminal contacting a coil spring located within the header, wherein the coil spring defines low contact force zones and high contact force zones relative to each other so that the high contact force zones apply a relatively higher force on a cylindrically shaped lead terminal inserted into the bore than the low contact force zones around a radius of the coil spring, wherein the coil spring is mounted within a housing groove on a housing within the header, and wherein the housing groove, in a cross-sectional plane which is perpendicular to a longitudinal axis of the bore, has a non-uniform radius around a circumference of the housing groove wherein a base of the groove includes a wall around a circumference of the groove, and radii extending from a center of the bore to the wall have varying lengths around the circumference in the cross-sectional plane which is perpendicular to the longitudinal axis of the bore.

19. The method of claim 18, wherein the housing groove defines an outer circumference having a non-circular shape.

20. The method of claim 18, further including applying a lubricant to the coil spring.

* * * * *